(12) United States Patent
Brosius

(10) Patent No.: US 7,244,121 B2
(45) Date of Patent: Jul. 17, 2007

(54) TORQUED TITANIUM-BASED ARCHWIRE

(76) Inventor: David J. Brosius, 3211 E. Longwood Dr., Crete, IL (US) 60417

( * ) Notice: Subject to any disclaimer, the term of this patent is extended or adjusted under 35 U.S.C. 154(b) by 162 days.

(21) Appl. No.: 11/028,698

(22) Filed: Jan. 4, 2005

(65) Prior Publication Data

US 2006/0147871 A1 Jul. 6, 2006

(51) Int. Cl.
*A61C 3/00* (2006.01)
(52) U.S. Cl. ........................................................ 433/20
(58) Field of Classification Search ................ 433/20, 433/8, 24
See application file for complete search history.

(56) References Cited

U.S. PATENT DOCUMENTS

| | | | |
|---|---|---|---|
| 2,566,414 A | 9/1951 | Henry | |
| 4,037,324 A | 7/1977 | Andreasen | |
| 4,818,226 A | 4/1989 | Berendt et al. | |
| 5,017,133 A | 5/1991 | Miura | |
| 5,137,446 A | 8/1992 | Yamauchi et al. | |
| 5,259,760 A | 11/1993 | Orikasa | |
| 5,464,347 A | 11/1995 | Allesee | |
| 5,683,245 A | 11/1997 | Scahdeva et al. | |
| 5,722,827 A | 3/1998 | Allesee et al. | |
| 6,036,489 A | 3/2000 | Brosius | |
| 6,736,637 B2 * | 5/2004 | Bond | 433/20 |

OTHER PUBLICATIONS

Highland Metals brochure which has entries on high torque NiTi arches (date uncertain, but prior to Feb. 28, 1994).

3M Unitek Catalog No. 16-851 9312, p. 5-13 which has entries on permachrome Henry Ideal Arches and permachrome Pretorqued, Preformed Edgewise Archwires (date uncertain, but believed to be Dec. 1993 due to "9312" designator in catalog number).

TP Orthodontics, Inc. 1995 Catalog, p. 85 which has an entry on stainless steel pretorqued archwire.

Ortho Specialties website page on S.E.T. Anterior Pre-Torqued Nickel Titanium Archwires (date uncertain, but prior to Jan. 4, 2004).

Materials from Wonder Wire regarding its Dual-Dimension Arches (date uncertain, but earliest fax header dated Apr. 22, 1995).

* cited by examiner

*Primary Examiner*—John J Wilson
(74) *Attorney, Agent, or Firm*—Leydig, Voit & Mayer, Ltd.

(57) ABSTRACT

A torqued archwire for use in an edgewise orthodontic bracket system. The archwire is substantially rectangular in cross-section, is made of titanium-based alloy and has a plurality of segments, including an anterior segment which is sized to cooperate with brackets attached to a person's central and lateral teeth. Positive torque is built into this anterior segment, with substantially the same positive torque being used across the entire length of the segment. Extending from the respective ends of the anterior segment are a pair of transition segments, in which the torque built into the archwire is approximately zero. Posterior segments of the archwire, which extend distally from the transition segments, each have a negative built-in torque, with substantially the same negative torque being used across the entire lengths of these segments. For ease of reference by an orthodontist, the "active" anterior segment of the archwire is laser etched or colored with non-toxic ink.

7 Claims, 2 Drawing Sheets

TORQUED TITANIUM-BASED ARCHWIRE

FIELD OF THE INVENTION

The present invention relates to orthodontic systems and appliances, and more particularly, to a titanium-based archwire having a positively torqued anterior section and a negatively torqued posterior section.

BACKGROUND OF THE INVENTION

Preadjusted and integrated "straight-wire" orthodontic bracket systems are well known, in which all the necessary angles and planes of movement—commonly referred to as "tip," "torque," "in-out" and "anti-rotation"—are manufactured directly into the brackets. These straight-wire appliances, when properly placed on teeth, are designed to allow the force and resilience of unbent archwires to work with the preadjustments to guide the teeth into ideal positions.

Contemporary appliance system designers strive to identify the proper position desired for each tooth at the conclusion of fixed appliance therapy (mechanotherapy), so that the individual brackets can be pre-built to provide, in conjunction with an archwire, theoretically appropriate alignment forces to the respective teeth. For example, if a designer desires seven degrees of crown torque, then a seven degree torque angle has typically been built into the individual edgewise bracket by well-known methods. The amount of torque actually expressed by a bracket, however, is dependent upon the wire-to-slot deviation angle—referred to as slot "play." Some play generally exists between any archwire and an edgewise bracket slot, even if the archwire is considered "full-size" relative to the slot. This play reduces the actual torque provided by the system from its full and theoretically correct expression.

To compensate for inadequate torque built into many preadjusted bracket systems, positive (+) crown torque is commonly added to the upper anterior segment of rectangular or square archwires late in treatment. Similarly, it may be desirable to apply a small amount of lingual or negative (−) crown torque to the lower anterior (i.e., central and lateral) teeth early in treatment to maintain their "upright" orientation.

These anterior-specific torque treatments are handled in various ways. Orthodontists most often add positive crown torque to the upper anterior segment by manually bending the torque into the anterior portion of individual stainless steel archwires. Titanium-based alloy archwires, particularly nickel titanium (nitinol) archwires, are generally considered to be ideal for orthodontics, especially in comparison to stainless steel, largely due to the low force these wires impart to crowns, coupled with their outstanding shape memory. This "superelasticity" is more biocompatible, meaning that there is less chance of damaging the dentition by moving crowns too quickly. Titanium-based wires also provide more complete correction without the need to constantly change archwires due to permanent deformation. It is virtually impossible, however, for an orthodontist to manually bend torque into titanium-based archwires due to this outstanding resistance to permanent deformation. This is why, for the critical final torque moments that are commonly bent into archwires, orthodontists are generally limited to the high forces and low shape memory of stainless steel, as opposed to the far more comfortable and biocompatible forces of nickel titanium or other titanium-based alloys.

For purposes of this invention, it will be understood that the term "titanium-based alloy" is intended to include nickel titanium alloys (with or without other elements, such as copper, columbium, iron or aluminum), beta titanium alloys and near-beta titanium alloys.

Manually bending torque into individual stainless steel archwires is a complex procedure that requires tremendous clinical skill and experience. Even substantial skill and experience do not assure an orthodontist that the desired torque will be imparted to the archwire or that the desired correction will occur precisely for each patient. Moreover, since an orthodontist is almost always directly responsible for manually torquing individual archwires, a great deal of "chairtime" is required.

In regard to applying lingual crown torque to the lower anterior teeth early in the treatment process, this is commonly attempted by using lower anterior brackets which have small amounts of torque built into them. Since small archwires allow for too much "play" in the bracket slots to express low levels of built-in bracket torque, "full-size" archwires are required if there is to be any meaningful expression of the desired lingual torque. But using a large edgewise wire early in treatment is not recommended, since the force provided is likely to be excessive and may cause biocompatibility problems (e.g., an overall reduction in the length of the root of the tooth, referred to as root "resorption"). Likewise, building more torque into the lower anterior brackets to compensate for the archwire play of small wires is not recommended, since problems could arise later in treatment when larger edgewise wires are employed, as they would then begin to express excessive amounts of lingual crown torque.

Because of these various difficulties in anterior-specific torque treatment, pretorqued archwires have been developed in which torque is built directly into the wire during manufacture. Pretorqued wires save valuable chairtime over manual wirebending (particularly since application of them can often be delegated to an orthodontic assistant as a routine wire change), they have greater biocompatibility (if titanium-based wire is used) and they theoretically provide more accurate results.

Currently, several types of pretorqued archwires are available to the orthodontist. One is a preformed stainless steel archwire. These wires have the drawbacks, however, of high force, resultant poor biocompatibility and low shape memory. Also, the built-in torque in all presently known steel versions extends through both the anterior and the posterior segments of the wire. It is not common to add torque to the upper posterior teeth, and it is usually very undesirable to increase torque in the lower posterior teeth. Consequently, the current pretorqued stainless steel archwires are seen as providing little improvement, if any, over the common art of manually bending wires, and they have had very little success in the marketplace.

Pretorqued nickel titanium archwires have also been introduced, but the earliest of these achieved little commercial success since they did not meet certain critical criteria. Specifically, the positive built-in torque was not limited to the anterior segment, as desired for proper treatment. Rather, positive torque also extended into the posterior area, where negative crown torque, if any, is most desirable. The transition from passive to torqued (active) wire should ideally occur in the area between the lateral and cuspid brackets (distal to the lateral bracket and mesial to the cuspid bracket), but in the first available nitinol pretorqued archwires this transition area was very broad, with the result that too little torque force was imparted to the lateral teeth and/or an undesirable (positive) torque force was imparted to some of the posterior teeth.

To address these problems, Ortho Specialties, Inc. of Hickory Hills, Ill., developed an improved, pretorqued archwire in which positive built-in torque was limited to a segment of the wire that, in use, corresponded to the brackets attached to anterior teeth. As described in U.S. Pat. Nos. 5,722,827 and 6,036,489 (assigned to Ortho Specialties), torque was built into the anterior segment, being maximized at the centerpoint and adjacent the central teeth brackets and then decreasing continuously along the remaining length of the anterior segment. The torque diminished to zero in transition segments between the corresponding adjacent lateral and cuspid brackets, and the posterior segments of the archwire (extending distally from the transition segments), generally included no built-in torque.

Over time, Ortho Specialties further modified this pretorqued archwire design so that substantially the same positive torque was built into the entire anterior segment, generally in the range of +10° to +50°, and preferably about +20°. As before, the posterior segments generally include no built-in torque. This archwire is manufactured for Ortho Specialties by Ultimate Wire Company of Bristol, Conn.

SUMMARY OF THE INVENTION

It is a primary object of the present invention to provide a still further improved torqued (i.e., pretorqued) archwire in which positive built-in torque is limited to a segment of the wire that, in use, corresponds to the brackets attached to anterior teeth, and in which a negative built-in torque is provided in the segments of the wire that, in use, correspond to the brackets attached to posterior teeth.

It is another object of this invention to provide an improved torqued archwire which is made of titanium-based alloy, such as nickel titanium, and thus has greater shape memory and is more biocompatible than stainless steel wire.

A further object of this invention is to provide a torqued archwire which has the positive active portion marked for ease of reference by an orthodontist.

Other objects and advantages of the invention will be apparent from the following detailed description.

In accordance with the present invention, there is provided a torqued archwire for use in an edgewise orthodontic bracket system. The archwire is an elongated member (i.e., either a single strand or a multi-strand braid) substantially rectangular in cross-section, is made of titanium-based alloy and has a plurality of segments, including an anterior segment which is sized to cooperate with brackets attached to a person's central and lateral teeth. Positive torque is built into this anterior segment, and is substantially the same along the entire length of the segment. Extending from the respective ends of the anterior segment are a pair of transition segments, generally corresponding with the patient's cuspids, in which the torque built into the archwire is approximately zero. Posterior segments of the archwire, which extend distally from the transition segments, include a negative built-in torque. For ease of reference by an orthodontist, the "active" anterior segment of the archwire is laser etched or colored with non-toxic ink.

BRIEF DESCRIPTION OF THE DRAWINGS

The detailed description particularly refers to the accompanying figures, in which.

DESCRIPTION OF THE PREFERRED EMBODIMENTS

Figure 1:
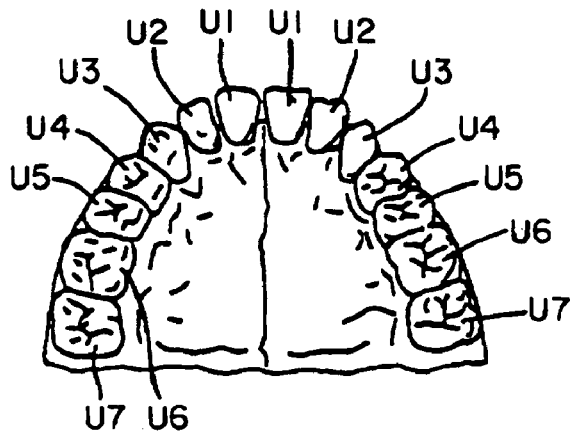
FIG. 1 is a plan view of a set of upper permanent teeth.
Figure 2:
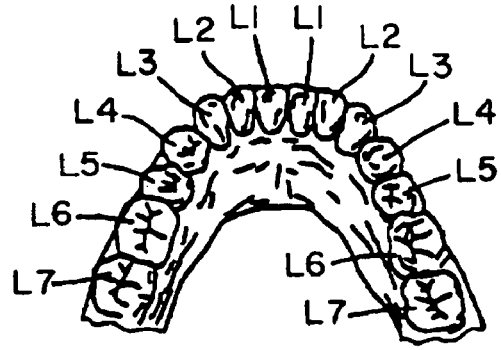
FIG. 2 is a plan view of a set of lower permanent teeth.

Turning now to the drawings and referring first to FIG. 1, there is shown a set of upper (maxillary) permanent teeth, including central teeth (labeled U1), lateral teeth (U2), cuspids (U3), first and second bicuspids (U4 and U5), and first and second molars (U6 and U7). Similarly, FIG. 2 illustrates a set of lower (mandibular) permanent teeth, including central teeth (labeled L1), lateral teeth (L2), cuspids (L3), first and second bicuspids (L4 and L5), and first and second molars (L6 and L7). The centrals and laterals, whether upper or lower, are known collectively as the anteriors.

Figure 3:
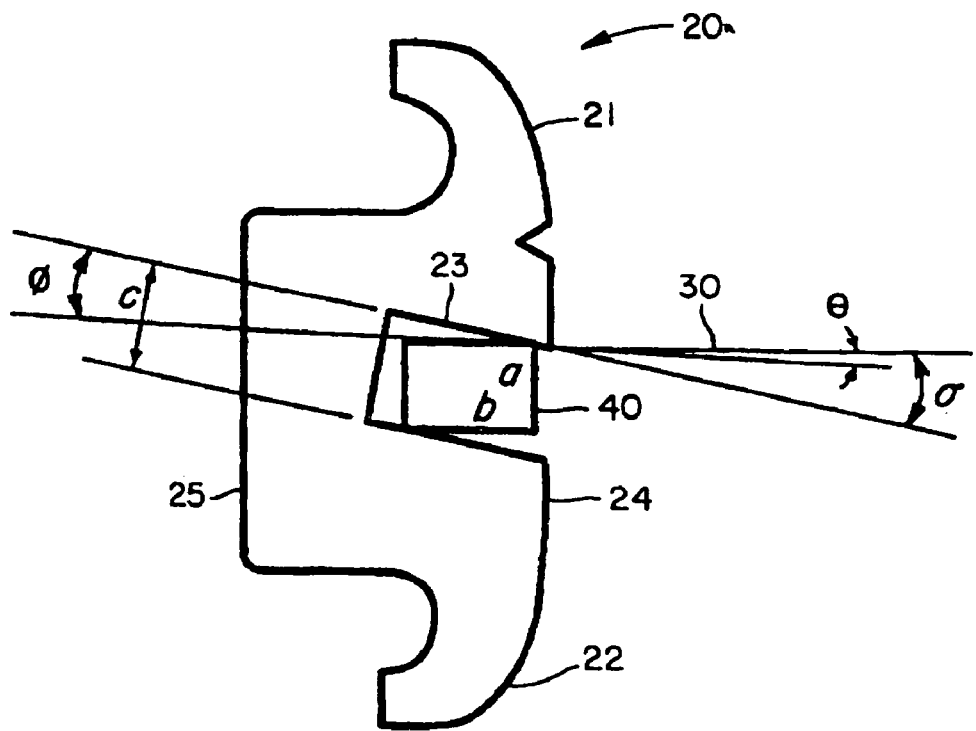
FIG. 3 is a cross-sectional view of an edgewise orthodontic bracket and an archwire, illustrating a plurality of variables used to calculate effective torque angles for an archwire assumed to be perfectly rectangular or square.

The present invention relates to preadjusted orthodontic bracket systems and methods for straightening upper and lower permanent teeth. More specifically, this invention is related to torque, which is also known to orthodontists as inclination or third order bends. Torque inclination is illustrated in FIG. 3. As is well known, an orthodontic bracket 20 includes tie wings 21, 22 and is formed to include a substantially rectangular-shaped slot 23. The bracket includes a front surface 24 and a rear surface 25 designed for attachment to a bonding pad or band, by means of which the bracket is secured on a particular tooth. Slot 23 is formed at a built-in angle C (known as the torque angle for bracket 20) relative to an imaginary line 30 perpendicular to the rear surface 25 of the bracket. Slot 23 is configured to edgewise receive a substantially rectangular cross-sectioned archwire 40. It should be noted for purposes of the present invention that the term "substantially rectangular archwire" is intended to include both rectangular and square archwire, as well as rectangular and square archwire having "rounded" or "beveled" corners.

The engagement between wire 40 and the side walls defining slot 23 applies a torque force to the tooth on which the bracket is mounted. Different torque angles are typically formed into the respective brackets for various teeth so as to apply a different torque force to each tooth. The built-in torque angle for each tooth depends upon the conventional orthodontic technique for which a bracket is designed.

The torque angle $\sigma$ and the slot width c of a bracket can be designed so that, when the bracket is used with a specifically-manufactured archwire, a conventional orthodontic technique may be replicated as to its theoretically desired embodiment accurately, predictably, efficiently and easily. This is due to precise consideration of the slot width and archwire dimensions (including corner radii) and of the actual torque forces generated. The magnitude of the actual torque forces applied to a tooth is based upon the torque angle $\sigma$ built into the respective bracket 20, the long cross-sectional dimension b and the short cross-sectional dimension a of the rectangular wire 40, and the width c of the archwire slot 23. The actual (or effective) torque force angle $\Theta$ is determined by subtracting "slot play" (i.e., the deviation angle φ) in a bracket/wire combination from the built-in torque angle σ. FIG. 3 illustrates these different angles.

The built-in torque angle σ is known (or can be readily determined) for a given bracket, and, if it is assumed that the archwire is perfectly square or rectangular, the deviation angle φ for the bracket/wire combination can be calculated by the formula:

$$\phi = \text{ARCSIN}\left[\frac{bc - a\sqrt{a^2 + b^2 - c^2}}{a^2 + b^2}\right]. \quad (1)$$

Thus, the effective torque angle Θ can be easily determined, since $$\Theta = \sigma - \phi. \quad (2)$$

Conversely, it will be appreciated that once the effective torque angle Θ recommended by a selected orthodontic technique is determined, and if the precise dimensions of a rectangular archwire and of a bracket slot are measured, then calculations can be made of both the deviation angle φ and the necessary built-in torque angle σ for achieving the effective torque angle.

The formula (1) above, which is based on an assumption of perfectly square or rectangular wire, has been supplemented with more accurate formulas that take into consideration wire corner rounding or beveling, which is common in available archwires. These formulas are discussed in commonly owned U.S. Pat. No. 5,820,370, which patent is hereby expressly incorporated by reference in its entirety.

Many commercial bracket systems are not designed to compensate for slot play. Instead, brackets are typically designed with the built-in torque angle σ matching the effective torque angle Θ prescribed by a particular orthodontic technique. As a result, because "full-sized" wires are not commonly used, the actual torque achieved is usually significantly less than prescribed.

The torqued archwire described herein compensates for the less-than-prescribed torque forces provided by the common usage of commercial bracket systems. Specifically, in accordance with an important aspect of the present invention, a rectangular titanium-based archwire is (a) positively torqued in a precisely defined anterior region such that, when it is used in conjunction with a commercial bracket system, additional positive torque force is applied to the anterior teeth, and (b) negatively torqued in the posterior regions such that, when used in conjunction with a commercial bracket system, additional negative torque is applied to the posterior teeth. Preferably, the torques built into the archwire should substantially correspond to, and compensate for, the slot play which results from insertion of the archwire into the slots of commercial anterior brackets.

Figure 4:
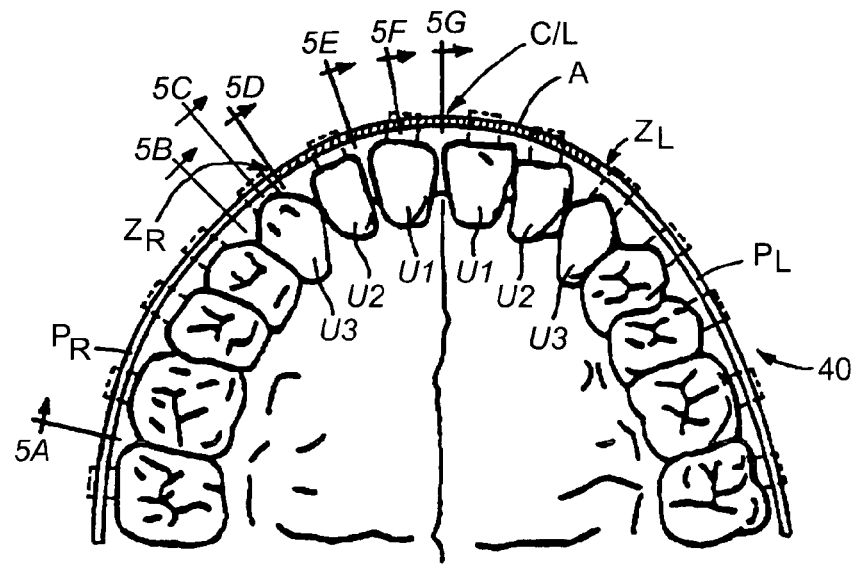
FIG. 4 is a plan view of an embodiment of the inventive torqued archwire shown relative to the set of upper permanent teeth illustrated in FIG. 1 and corresponding brackets (representationally illustrated in phantom)

Turning now to FIG. 4, there is shown an embodiment of the inventive torqued archwire 40 depicted in relation to the set of upper permanent teeth of FIG. 1 and corresponding edgewise brackets (shown in phantom). The archwire has a positively torqued active region (A), which overlaps the brackets attached to the four anterior teeth (U1, U2) and is identified, on at least one of its surfaces, by laser etching or a colored coating of non-toxic FDA white-listed ink (the hatched region in FIG. 4). At the two distal ends ($Z_L$, $Z_R$) of the active region, the built-in torque transitions to zero. It is in the two transition regions (which correspond approximately to the zones of contact with the brackets on the patient's cuspids (U3)) where the transitions from the positively torqued active region to the negatively torqued posterior regions ($P_L$, $P_R$) occur. Each posterior region is preferably negatively torqued in an equal amount along its entire length, although small (and clinically insignificant) differences in negative torque can exist due to unavoidable manufacturing tolerances (±2°). In accordance with a preferred embodiment, the negative torque across these posterior regions is approximately −20°, but depending upon the patient's needs may be any value within the range of −5° to −35°.

In the present invention, the positive torquing of the archwire's anterior region begins precisely at the "zero" points ($Z_L$, $Z_R$), which are formed in the archwire a predetermined arcuate distance from one another, depending upon the desired "size" of the wire. Since the populace includes persons having different archwidths, it is desirable to provide archwires having active regions of various lengths (i.e., sizes). Active region lengths over a range of about 24–40 mm would be adequate to accommodate almost all persons, and the assignee of this invention, Ortho Specialties, presently markets torqued nitinol archwires having three different active region lengths—28 mm, 34 mm and 38 mm. For any given person, an appropriately-sized torqued archwire should be long enough that, upon insertion into the edgewise bracket slots, each of its "zero" points lies in the space between brackets attached to corresponding adjacent lateral and cuspid teeth.

Referring again to FIG. 4 and considering the "active" region between the two "zero" points, the amount of positive torque built into the archwire remains substantially the same, including across the centerline (C/L) of the active region. This centerline of the archwire, which is typically identified by a visual indicator (such as a scribe line or a small ink mark), is intended to be positioned in the space between the brackets on the two central teeth (U1) during treatment. The positive torque at the centerline and across the central and lateral teeth (U1, U2) is preferably about 20°, but depending upon the patient's needs may be any value within the range of 5° to 35°.

Figure 5:
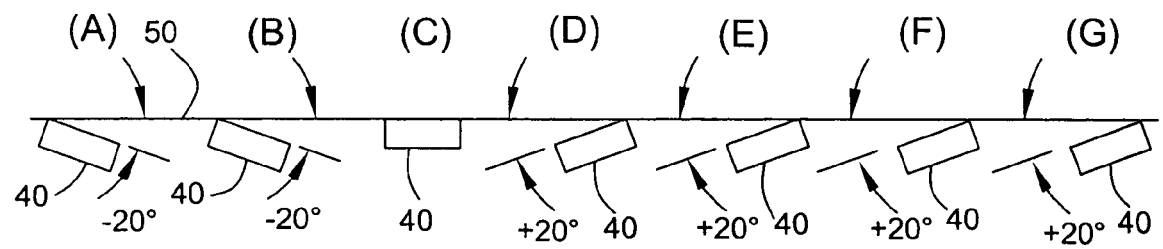
FIGS. 5A through 5G are enlarged, cross-sectional views of the archwire of FIG. 4 taken, respectively, along the lines 5A through 5G, illustrating those views in angular relation to an imaginary plane.

FIGS. 5A–5G show several enlarged, cross-sectional views of the torqued archwire of FIG. 4, taken at various points along one half of the wire (beginning in the right posterior region ($P_R$) and proceeding mesially to the centerline (C/L)). In FIG. 5A, the archwire is negatively torqued (preferably about −20°). FIG. 5B is taken at a point just distal to the cuspid bracket, and accordingly is still negatively torqued (again, preferably about −20°). FIG. 5C is taken across the intersection of the archwire with the cuspid bracket, where the torque is preferably zero, and thus the archwire here defines an imaginary torque plane 50 against which the other cross-sectional views can be angularly compared. FIG. 5D is taken at a point just mesial to the "zero" point. Here the built-in torque is about 20° in the preferred embodiment. In the cross-section of FIG. 5E, taken at a point approximately midway between the "zero" point and the centerline, the torque remains at about 20°. Likewise, FIG. 5F shows that the torque at a point corresponding to the bracket on the central tooth remains the same at about 20°. Finally, at the centerline of the archwire, as shown in FIG. 5G, the built-in torque is also about 20°.

Although not illustrated, it will be appreciated that the inventive archwire is designed so that the torques along the left half of the archwire essentially mirror the right half torques shown in FIGS. 5A–5G.

Preferred embodiments of this invention are described herein, including the best mode known to the inventors for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. An archwire of substantially rectangular cross-section which, in conjunction with a set of orthodontic brackets having slots to edgewise receive the archwire, applies torque forces to selected teeth, the archwire comprising:
    a continuous, elongated member of titanium-based alloy formed to have a plurality of segments, including,
    a curved anterior segment having a centerpoint,
        which segment upon insertion into corresponding bracket slots, extends substantially parallel to the four central and lateral teeth with the centerpoint positioned between the brackets on the two central teeth;
    first and second transition segments, each extending distally from a respective end of the anterior segment; and
    first and second posterior segments extending distally from, respectively, the distal ends of the first and second transition segments;
    wherein the anterior segment has a positive built-in torque which is substantially the same over the length of the segment each of the posterior segments has a negative built-in torque which is substantially the same over the length of the segment and each transition segment, upon insertion of the archwire into the bracket slots, is positioned corresponding to a bracket on a cuspid tooth, the transition segments each having approximately 0° built-in torque.

2. The archwire of claim 1, wherein the positive built-in torque in the anterior segment is in a range of about 5° to 35°.

3. The archwire of claim 1, wherein the positive built-in torque in the anterior segment is approximately 20°.

4. The archwire of claim 1, wherein the negative built-in torque in each posterior segment is in a range of about −5° to 35°.

5. The archwire of claim 1, wherein the negative built-in torque in each posterior segment is approximately −20°.

6. The archwire of claim 1, wherein the portion of the wire comprising the anterior segment is marked with non-toxic ink.

7. The archwire of claim 1, wherein the portion of the wire comprising the anterior segment is marked by laser etching.

* * * * *